(12) United States Patent
Klemm et al.

(10) Patent No.: US 11,291,817 B2
(45) Date of Patent: Apr. 5, 2022

(54) MEDICAMENT DELIVERY DEVICE

(71) Applicant: SANOFI, Paris (FR)

(72) Inventors: Thomas Klemm, Frankfurt (DE); Dietmar Hammen, Frankfurt (DE)

(73) Assignee: Sanofi, Paris (FR)

( * ) Notice: Subject to any disclaimer, the term of this patent is extended or adjusted under 35 U.S.C. 154(b) by 220 days.

(21) Appl. No.: 16/471,451

(22) PCT Filed: Dec. 21, 2017

(86) PCT No.: PCT/EP2017/084145
§ 371 (c)(1),
(2) Date: Jun. 19, 2019

(87) PCT Pub. No.: WO2018/115311
PCT Pub. Date: Jun. 28, 2018

(65) Prior Publication Data
US 2021/0100993 A1    Apr. 8, 2021

(30) Foreign Application Priority Data
Dec. 23, 2016  (EP) ..................... 16206616

(51) Int. Cl.
*A61M 37/00* (2006.01)
*A61M 5/142* (2006.01)
(52) U.S. Cl.
CPC .... *A61M 37/0015* (2013.01); *A61M 5/14248* (2013.01); *A61M 2037/0007* (2013.01); *A61M 2037/0023* (2013.01); *A61M 2205/3306* (2013.01); *A61M 2205/3317* (2013.01); *A61M 2205/3331* (2013.01)

(58) Field of Classification Search
CPC .......... A61M 37/0015; A61M 5/14248; A61M 2037/0007; A61M 2037/0023; A61M 2205/3306; A61M 2205/3317; A61M 2205/3331; A61M 5/1684; A61M 5/16854; A61M 2205/3334; A61M 2205/3561; A61M 2205/50; A61M 5/16809;
(Continued)

(56) References Cited

U.S. PATENT DOCUMENTS 5,713,865 A    2/1998  Manning et al.
2003/0083645 A1  5/2003  Angel et al.
(Continued)

FOREIGN PATENT DOCUMENTS

CN    1551786     12/2004
CN    101132734    2/2008
(Continued)

OTHER PUBLICATIONS

International Search Report and Written Opinion in International Appln. No. PCT/EP2017/084145, dated Mar. 5, 2018, 10 pages.
(Continued)

*Primary Examiner* — Amber R Stiles
(74) *Attorney, Agent, or Firm* — Fish & Richardson P.C.

(57) ABSTRACT

A medicament delivery device comprises a delivery assembly for transdermally delivering medicament to a patient and a system for providing information on the volume of medicament in the device. The system comprises a sensing unit configured to measure at least one physical parameter dependent on the volume of medicament in the device.

13 Claims, 10 Drawing Sheets

(58) Field of Classification Search
CPC ...... A61M 5/1452; A61M 2005/14204; A61M 2205/3379; A61M 2005/14268
See application file for complete search history.

(56) References Cited

U.S. PATENT DOCUMENTS

| | | |
|---|---|---|
| 2004/0162470 A1 | 8/2004 | Tu |
| 2008/0154187 A1 | 6/2008 | Krulevitch et al. |
| 2009/0069756 A1 | 3/2009 | Larsen |
| 2009/0118667 A1 | 5/2009 | Haueter et al. |
| 2009/0259176 A1* | 10/2009 | Yairi .................. A61M 35/10 604/67 |
| 2011/0112473 A1 | 5/2011 | Bochenko et al. |
| 2011/0160652 A1* | 6/2011 | Yodfat .............. A61M 5/14248 604/66 |
| 2013/0204227 A1* | 8/2013 | Bochenko ............... A61M 5/31 604/506 |
| 2014/0171869 A1 | 6/2014 | Zhang |
| 2015/0045727 A1 | 2/2015 | Bammer et al. |
| 2015/0080844 A1* | 3/2015 | Donovan .......... A61M 5/16854 604/505 |
| 2015/0268656 A1 | 9/2015 | Bammer et al. |

FOREIGN PATENT DOCUMENTS

| | | |
|---|---|---|
| CN | 101437558 | 5/2009 |
| CN | 103933641 | 7/2014 |
| EP | 1818664 | 8/2007 |
| JP | H08-320248 | 12/1996 |
| JP | 2002-126077 | 5/2002 |
| JP | 2002-239000 | 8/2002 |
| JP | 2005-525141 | 8/2005 |
| JP | 2009-525770 | 7/2009 |
| JP | 2009-529999 | 8/2009 |
| JP | 2012-532717 | 12/2012 |
| JP | 2014-087450 | 5/2014 |
| JP | 2015-512509 | 4/2015 |
| JP | 2015-096098 | 5/2015 |
| JP | 2015-532136 | 11/2015 |
| WO | WO 2003/020345 | 3/2003 |
| WO | WO 2003/037403 | 5/2003 |
| WO | WO 2006/077578 | 7/2006 |
| WO | WO 2007/107558 | 9/2007 |
| WO | WO 2007/130868 | 11/2007 |
| WO | WO 2011/005880 | 1/2011 |
| WO | WO 2011/006920 | 1/2011 |
| WO | WO 2013/138830 | 9/2013 |
| WO | WO 2014/052997 | 4/2014 |
| WO | WO 2014/152704 | 9/2014 |

OTHER PUBLICATIONS

International Preliminary Report on Patentability in International Appln. No. PCT/EP2017/084145, dated Jun. 25, 2019, 7 pages.

* cited by examiner

MEDICAMENT DELIVERY DEVICE

CROSS REFERENCE TO RELATED APPLICATIONS

This application is a U.S. national stage application under 35 USC § 371 of International Application No. PCT/EP2017/084145, filed on Dec. 21, 2017, which claims priority to European Application No. 16206616.1, filed on Dec. 23, 2016, the entire contents of which are incorporated herein by reference.

TECHNICAL FIELD

The present disclosure relates to a device for delivery of medicament to a patient.

BACKGROUND

A variety of diseases exists that require regular treatment by injection of a medicament. Such injection can be performed by using hypodermic injection devices, which are applied either by medical personnel or by patients themselves. As an example, type-1 and type-2 diabetes can be treated by injection of insulin doses, for example once or several times per day, using an insulin injection device. This type of devices typically comprises an insulin pump connected to a cannula or a hypodermic injection needle through which the insulin can flow towards the patient's skin. Transdermal delivery devices are an alternative to hypodermic injection devices.

SUMMARY

In some aspects, a medicament delivery device includes a delivery assembly having a plurality of microneedles configured to transdermally delivering medicament to a patient, and a system for providing information on the volume of medicament in the device. The system includes a sensing unit configured to measure at least one physical parameter dependent on the volume of medicament in the device.

The sensing unit may include a first electrode and a second electrode arranged to form a capacitor, the first and second electrodes being configured such that, in use, medicament flows between the first and second electrodes, wherein the sensing unit may further include a current source connected to the first and second electrodes and configured to generate a voltage between the first and second electrodes.

The current source may be a direct current source and the sensing unit may be configured to measure the capacitance of the capacitor formed by the first and second electrodes so that the system can determine information on the volume of medicament between the first and second electrodes based on the capacitance measured.

The current source may be a direct current source and the sensing unit may be configured to measure the resistance of the medicament between the first and second electrodes so that the system can determine information on the volume of medicament between the first and second electrodes based on the resistance measured.

The current source may be an alternating current source and the sensing unit may be configured to measure the impedance of the medicament between the first and second electrodes so that the system can determine information on the volume of medicament between the first and second electrodes based on the impedance measured.

The system may be configured to determine information on the volume of medicament in the device by optical sensing.

The system may include a light source, an optical detector, and a generally funnel-shaped passage through which, in use, medicament can flow, wherein, in use, the light source may be configured to emit light towards the passage filled with medicament, wherein the detector may be configured to detect light transmitted by the medicament in the passage, and the system may be configured to determine information on the volume of medicament in the device based on the amount of light detected by the detector.

The system may be configured to determine information on the volume of medicament in the device by pressure sensing.

The medicament delivery device may include a porous membrane for retaining the medicament.

The porous membrane may be disposed between the first and second electrodes.

The generally funnel-shaped passage may be located in the porous membrane.

The medicament delivery device may include a medicament pump mechanism for pumping the medicament towards the delivery assembly.

The medicament pump mechanism may be configured to operate in accordance with information on the volume of medicament in the device provided by the system.

The medicament delivery device may include a cartridge of medicament.

The medicament delivery device may include an indicator configured to provide to a user information on the volume of medicament in the device based on the measured physical parameter. The indicator may be configured to indicate to the user when the volume of medicament in the device falls below a predetermined value.

The medicament delivery device may include a reusable part and a disposable part, and the medicament pump mechanism may be located in the reusable part.

The medicament delivery device may be a wearable device. The medicament delivery device may include a bottom surface configured to removably attach to the patient's skin.

The medicament delivery device may include a wireless communication unit configured to transmit and/or receive information to/from another device in a wireless fashion. The wireless communication unit may be configured to transmit information on the volume of medicament remaining in the device to another device in a wireless fashion.

The medicament delivery device may include a controller for controlling the medicament delivery to the patient.

The medicament delivery device may include an insulin delivery device. The medicament delivery device may include a blood glucose sensor configured to send data relating to the blood glucose of the patient to the controller so that the controller controls the insulin delivery to the patient.

According to a further aspect, there is provided a method of providing information on the volume of medicament in a medicament delivery device, the medicament delivery device comprising a delivery assembly for transdermally delivering medicament to a patient and a system for providing information on the volume of medicament in the device, the system comprising a sensing unit, the method comprising using the sensing unit to measure at least one physical parameter dependent on the volume of medicament in the device.

The sensing unit may include a first electrode and a second electrode arranged to form a capacitor, the first and second electrodes being configured such that, in use, medicament flows between the first and second electrodes, the sensing unit may further include a current source connected to the first and second electrodes, and the method may include using the current source to generate a voltage between the first and second electrodes The current source may be a direct current source and the method may include using the sensing unit to measure the capacitance of the capacitor formed by the first and second electrodes, and using the system to determine information on the volume of medicament between the first and second electrodes based on the capacitance measured The current source may be a direct current source and the method may include using the sensing unit to measure the resistance of the medicament between the first and second electrodes, and using the system to determine information on the volume of medicament between the first and second electrodes based on the resistance measured.

The current source may be an alternating current source and the method may include using the sensing unit to measure the impedance of the medicament between the first and second electrodes, and using the system to determine information on the volume of medicament between the first and second electrodes based on the impedance measured.

The method may include using the system to determine information on the volume of medicament in the device by optical sensing.

The method may include using the system to determine information on the volume of medicament in the device by pressure sensing.

The method may include determining the flow rate of the medicament to be delivered depending on patient data.

The method may include measuring pressure of medicament in the device prior to the medicament delivery to the patient.

The method may include comparing the volume of medicament determined to expected values.

The method may include monitoring the medicament delivery to the patient to avoid the device running out of medicament.

The method may include transmitting information on the volume of medicament remaining in the device to another device in a wireless fashion to avoid the device running out of medicament.

The method may include communicating with another device in a wireless fashion to order medicament prescription if the volume of medicament determined falls below a predetermined value.

The method may include communicating with another device in a wireless fashion dosage regimen and/or medicament concentration. The method may comprise determining how long until medicament is needed based on the received dosage regime and/or medicament concentration information.

The transdermal medicament delivery device may provide a less painful, non-invasive medicament delivery that may be more easily carried out by the patients themselves. The medicament delivery device may also reduce irritation when delivering medicament for long periods of time. Further, the transdermal medicament delivery device may reduce tissue damage. An indication of the level of medicament remaining in the medicament delivery device may reduce errors in use by notifying the user when the device is running out of medicament, or when an occlusion or a leak occurs in the device.

The terms "drug" or "medicament" which are used interchangeably herein, mean a pharmaceutical formulation that includes at least one pharmaceutically active compound.

The term "medicament delivery device" shall be understood to encompass any type of device, system or apparatus designed to immediately dispense a drug to a human or non-human body (veterinary applications are clearly contemplated by the present disclosure). By "immediately dispense" is meant an absence of any necessary intermediate manipulation of the drug by a user between discharge of the drug from the drug delivery device and administration to the human or non-human body. Without limitation, typical examples of drug delivery devices may be found in injection devices, inhalers, and stomach tube feeding systems. Again, without limitation, exemplary injection devices may include, e.g. patch devices, autoinjectors, injection pen devices, and spinal injection systems.

BRIEF DESCRIPTION OF THE FIGURES

Exemplary embodiments are described with reference to the accompanying drawings, in which.

DETAILED DESCRIPTION

This disclosure relates to a medicament delivery device comprising a delivery assembly for transdermally delivering medicament to a patient, and a system for providing information about the volume of medicament in the device. The system comprises a sensing unit configured to measure at least one physical parameter dependent on the volume of medicament in the device. Providing such a medicament delivery device may help towards avoiding the use of an injection needle for delivering the medicament to the patient. Since the medicament is delivered transdermally, no injection needle is needed. Therefore, such a medicament delivery device does not require a needle hole to be created at the injection site and so can help towards avoiding tissue injury, as well as helping to reduce pain and discomfort in the medicament delivery process. In addition, irritations and complications that may occur by introduction and/or presence of a needle into the skin in a conventional needle injection device may be avoided. Furthermore, the system for providing information on the volume of medicament in the device allows a user or patient to detect when the device is running out of medicament, or to detect when an occlusion or a leak occurs in the device, so that the user or patient can take the appropriate action.

Figure 1:
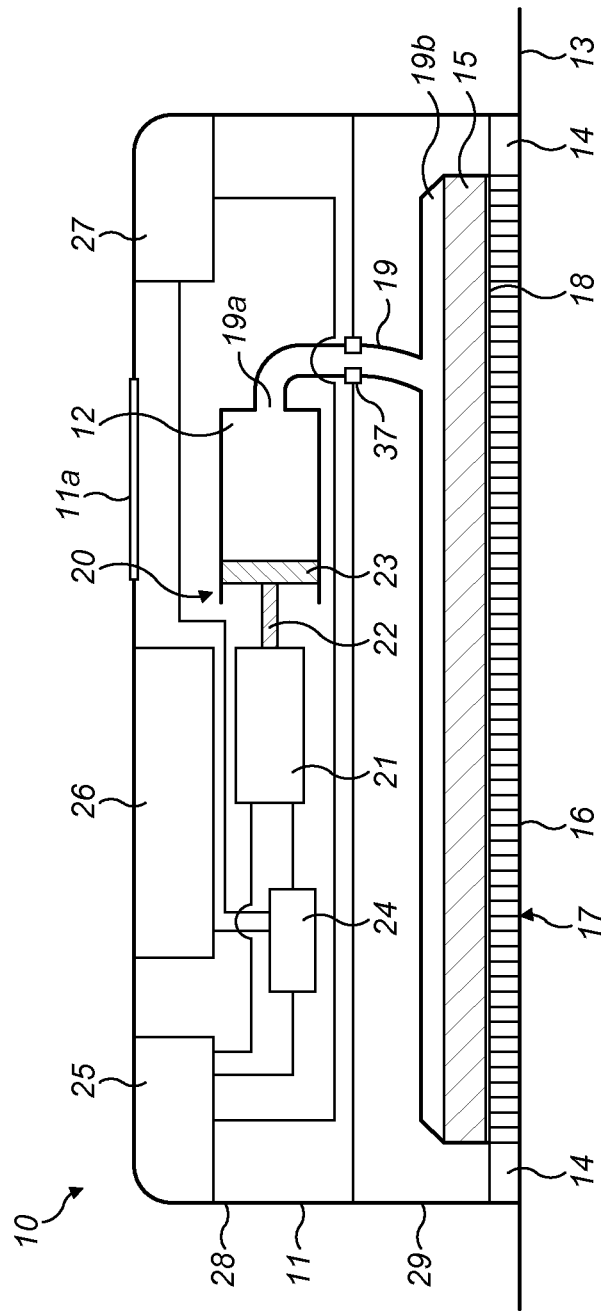
FIG. 1 is a schematic cross-sectional view of a medicament delivery device, which may include embodiments.

According to some embodiments of the present disclosure, an exemplary drug delivery device 10, herein simply referred to as "device 10", is shown in FIG. 1.

In the context of this application, the terms "upstream" and "downstream" are used herein in relation to the direction of medicament flow through the device in normal use. Moreover, the terms "upper", "lower" and so forth are used herein in relation to the orientation of the device shown in the accompanying drawings.

The drug delivery device, as described herein, may be configured to inject a medicament into a patient. Such a device could be operated by a patient or care-giver, such as a nurse or physician. The device includes a large volume device ("LVD") or patch pump, configured to adhere to a patient's skin for a period of time (e.g., about 5, 15, 30, 60, 120 minutes or longer) to deliver a "large" volume of medicament (typically about 2 ml to about 10 ml or more).

In combination with a specific medicament, the presently described device may also be customized in order to operate within required specifications. For example, the device may be customized to inject a medicament within a certain time period (e.g. about 10 minutes to about 60 minutes or longer). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP.

The delivery devices described herein can also include one or more automated functions. For example, the medicament injection can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of the present drug delivery device may each be activated via an activation mechanism. Such an activation mechanism can include one or more of a button, a lever or other activation component. Activation of an automated function may be a one-step or multi-step process. That is, a user may need to activate one or more activation components in order to cause the automated function. For example, in a one-step process, a user may depress a button or interact with a user interface in order to cause injection of a medicament. Other devices may require a multi-step activation of an automated function.

Referring to FIG. 1, the device 10 includes a body or housing 11 which typically contains a medicament reservoir 12 or cartridge pre-filled with liquid medicament to be injected, and the components required to facilitate one or more steps of the delivery process. The device 10 can include a cover or lid 11a, which can be removed when the reservoir 12 (medicament cartridge) needs to be changed or refilled. The device 10 can also include a protective cover 13 that can be detachably adhered to a bottom surface of the device 10. Typically, when using the device 10 for the first time, a user must remove the protective cover 13 from the housing 11 before the device 10 can be operated.

The device 10 is intended to be placed on the skin of the patient, e.g. on the abdomen of the patient. The device 10 is preferably a wearable device. Such devices are commonly referred to as "patch pumps" or "skin patches" due to their nature of being worn or affixed to the patient's skin. The device 10 comprises a device holding element 14 e.g. in the form of an adhesive tape or adhesive pad 14 configured to adhere to the patient's skin. The adhesive pad 14 is attached to the bottom side or skin attachment side of the device 10 and covered by the protective cover 13 prior to the first use of the device 10. The adhesive pad 14 ensures the adhesion of the device 10 onto the skin so that in use, the device 10 does not detach from the skin. Alternatively, the device 10 comprises a device-holding element operating with vacuum to adhere the device 10 to the skin.

The device 10 includes a medicament receiving element configured to receive the medicament flowing from the medicament reservoir 12. In the embodiment described herein, the medicament-receiving element is in the form of a porous membrane, e.g. a fleece or absorbent pad 15. The absorbent pad 15 allows for a substantially continuous controlled delivery of the medicament to the patient.

The device 10 further comprises a delivery assembly 17 for transdermally delivering medicament to a patient. The delivery assembly 17 comprises a plurality of microneedles 16 arranged in an array. The delivery assembly 17 is configured to transdermally deliver medicament to the patient. The microneedles 16 are disposed downstream of the absorbent pad 15, and are configured to deliver to the patient the medicament flowing from the absorbent pad 15. The microneedles 16 extend substantially downwardly from a structure or support 18. The support 18 may be made from a rigid or flexible sheet of metal or plastic. The support 18 is perforated so that medicament can flow through the support 18 towards the microneedles 16. It should be understood that the number of microneedles 16 shown in the Figures is for illustrative purposes only. The actual number of microneedles 16 used in the device 10 may, for example, range between around 70 and around 7000 microneedles, depending on the area of the bottom surface of the device 10. The size and shape of the microneedles 16 may also vary as desired. For example, the microneedles 16 may have an overall conical shape, an overall pyramidal shape or a cylindrical portion upon which is positioned a conical portion having a tip. The microneedles 16 are typically of a length sufficient to penetrate the stratum corneum and pass into the epidermis. In certain embodiments, the microneedles 16 have a length ranging between around 0.2 and around 3 millimeters. The microneedles 16 help to overcome the skin barrier by creating pores in the skin, thereby enhancing the penetration of the medicament through the skin. The microneedles 16 perforate the outer skin layer and ensure that the medicament diffuses in the pores thereby created. The uptake of the medicament through the skin works by diffusion, i.e. the medicament flows down a gradient of concentration, from the absorbent pad 15 towards the patient's skin. Once absorbed, the medicament is transported into the blood e.g. with the lymph. The medicament uptake by the patient's body via microneedles has been shown to be better than subcutaneously, e.g. via a hypodermic injection needle, in particular in the case of insulin.

The device 10 comprises a tube or hose dispatcher or manifold 19 in fluid communication with the medicament reservoir 12. The manifold 19 includes an inlet 19a connected to the medicament reservoir 12 and a dispense outlet 19b connected to the absorbent pad 15. The manifold 19 is arranged such that, in use, medicament flows from the medicament reservoir 12 through the manifold 19 via the inlet 19a, and towards the absorbent pad 15 via the dispense outlet 19b. The manifold 19 is sealingly connected to the medicament reservoir 12 to ensure that the medicament is kept sterile and to avoid leaks of medicament. The dispense outlet 19b is disposed upstream of the absorbent pad 15 and is configured such that medicament flowing from the manifold 19 is distributed substantially uniformly in the absorbent pad 15. For example, and as visible in FIG. 1, the absorbent pad 15 faces the dispense outlet 19b and the area of the absorbent pad 15 is substantially similar to the area of the cross-section of the dispense outlet 19b.

A pump mechanism 20 is provided to cause the medicament to flow from the medicament reservoir 12 through the manifold 19. The pump mechanism 20 includes a motor 21, a thumb screw 22, and a plug or piston 23. In use, the motor 21 rotates the thumb screw 22, which drives the piston 23 within the medicament reservoir 12 towards the manifold 19. While driven by the motor 21, the piston 23 pushes the medicament out of the reservoir 12 through the manifold 19 via the inlet 19a, and towards the absorbent pad 15 via the dispense outlet 19b. The absorbent pad 15 allows for a uniform distribution of the medicament and therefore ensures that the medicament is homogeneously distributed on the delivery assembly 17 (array). The medicament flows from the absorbent pad 15 through the delivery assembly 17 (array) of microneedles 16, and diffuses through the skin.

The device 10 further comprises a controller 24 for monitoring and/or controlling the operation of the device 10. The controller 24 includes memories such as a Random Access Memory and/or a Read-Only Memory, and a firmware configured to control the motor 21 such that the flow or amount of medicament delivered can be varied, e.g. so that the medicament is pumped at a rate which enables the skin to absorb the medicament. The device 10 also comprises a power supply 25, a user interface 26, and a wireless communication unit 27.

Figure 2:
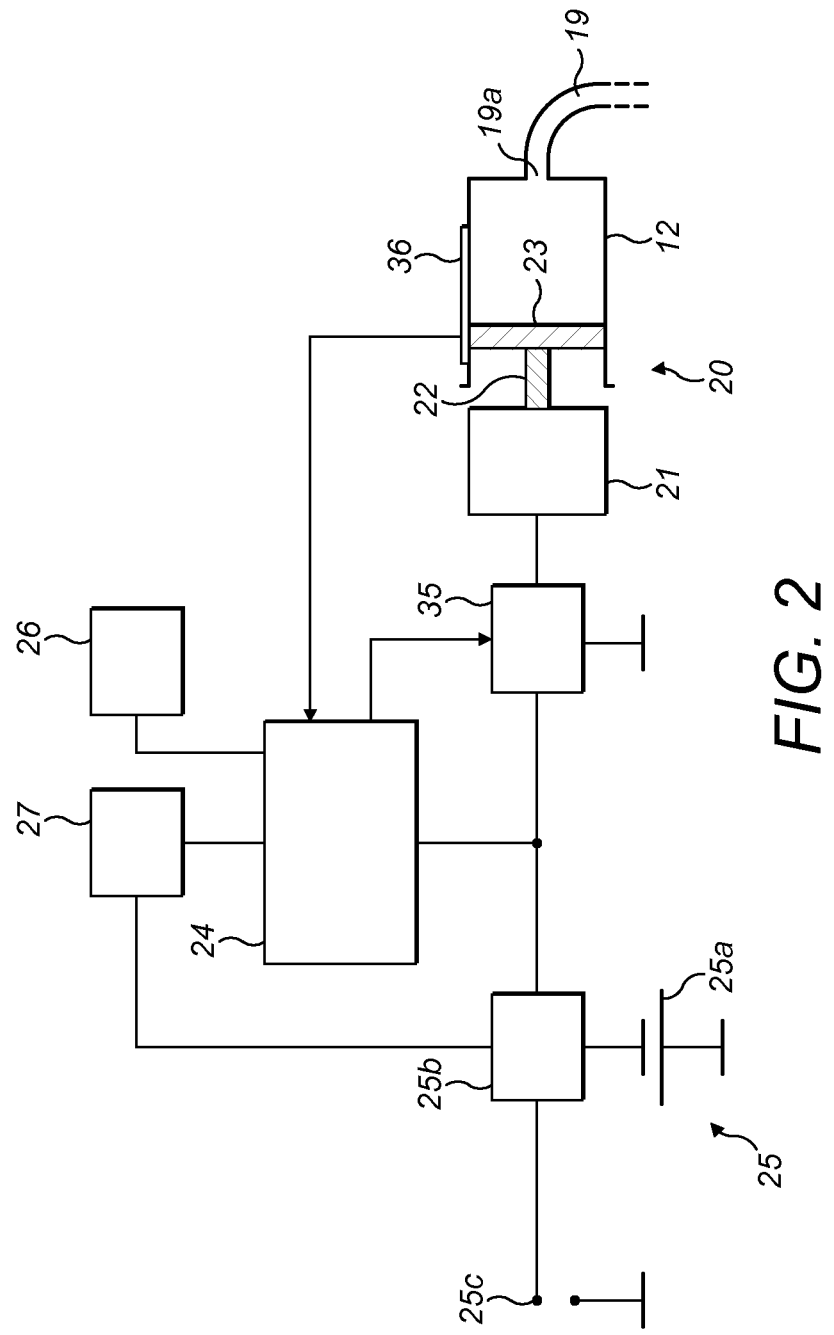
FIG. 2 is a block diagram of a part of the medicament delivery device of FIG. 1.

FIG. 2 is a block diagram schematically showing the electronic components of the device 10 of FIG. 1. The power supply 25 includes a disposable or rechargeable battery 25a, a power controller 25b, and a supply contact 25c. The supply contact 25c is configured to enable the device 10 to be connected to an external power source for powering the device 10 or for recharging the battery 25a. The power supply 25 is connected to the controller 24 and to the wireless communication unit 27 to supply power to each.

The power supply 25 is connected to the motor 21 via a pulse-width modulator 35 for powering the motor 21. The controller 24 is connected to the pulse width modulator 35 to control the drive of the motor 21. The controller 24 is also connected to the wireless communication unit 27 and with the user interface 26 to control and receive signal input from each. The pump mechanism 20 and/or reservoir 12 comprise an encoder 36, such as a linear transducer. The encoder 36 is connected to the controller 24 and is configured to send a signal indicative of the position of the piston 23 to the controller 24. Alternatively, or in addition, the encoder 36 is a rotational transducer and is configured to send a signal indicative of the number of rotations of the thumb screw 22 to the controller 24. The controller 24 and the pulse-width modulation 35 are powered by the power supply 25.

The wireless communication unit 27 is configured to transmit and/or receive information to/from another device in a wireless fashion. Such transmission may for instance be based on radio transmission or optical transmission. In some embodiments, the wireless communication unit 27 is a Bluetooth transceiver or NFC transceiver. Alternatively, the wireless communication unit 27 may be substituted or complemented by a wired unit configured to transmit and/or receive information to/from another device in a wire-bound fashion, for instance via a cable or fiber connection. When data is transmitted, the units of the data (values) transferred may be explicitly or implicitly defined. For instance, in case of an insulin dose, always International Units (IU) may be used, or otherwise, the used unit may be transferred explicitly, for instance in coded form.

Figure 3:
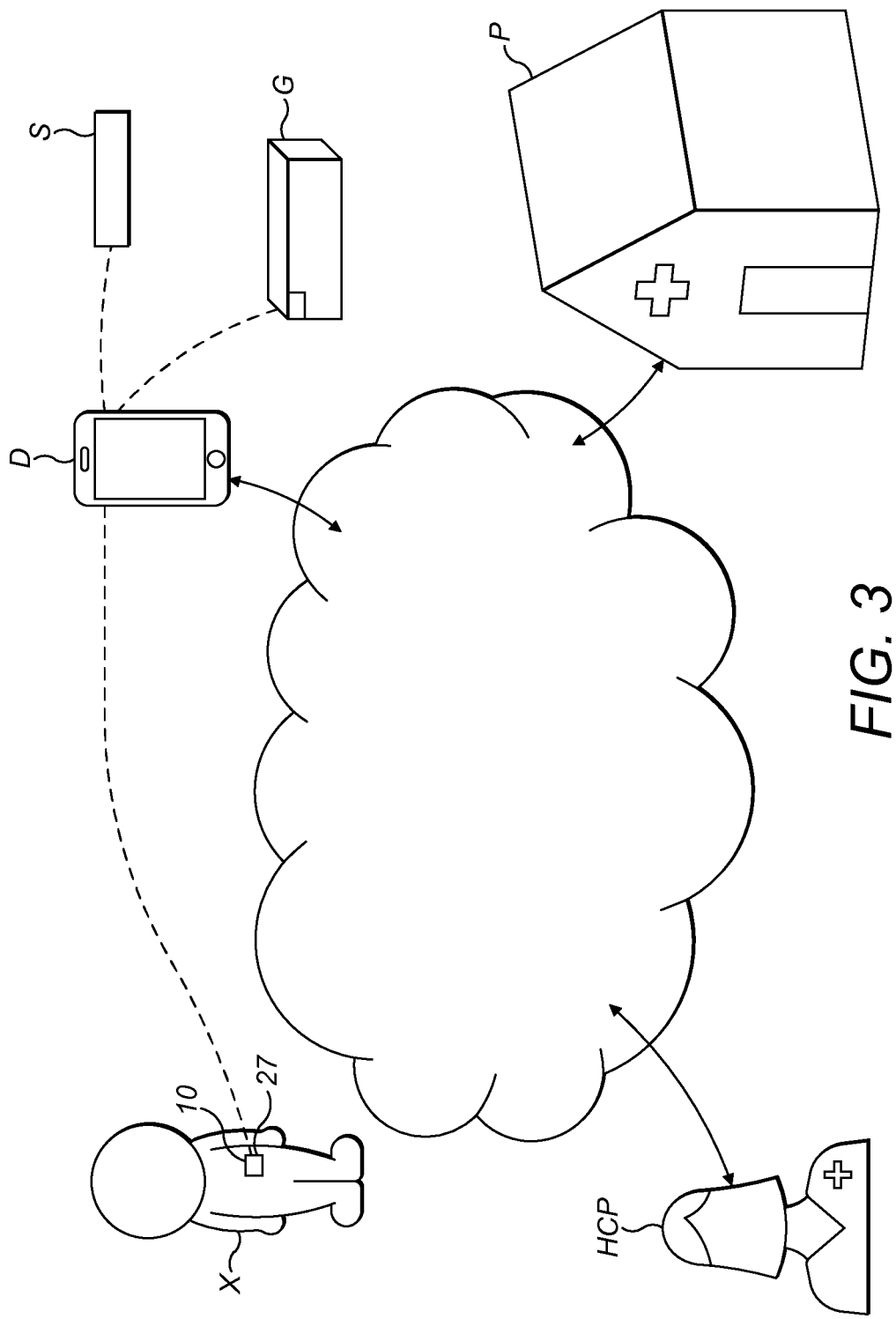
FIG. 3 is a diagram showing a medicament delivery device, in wireless connection with various devices.

The controller 24 may be programmed to cause a flow of medicament through the manifold 19 towards the patient's skin based on instructions from a separate, remote device. As illustrated in FIG. 3, the wireless communication unit 27 may be configured to receive instructions from a remote device D, such as a smartphone or tablet running a specific application. The wireless communication unit 27 is configured to deliver the received instructions to the controller 24. In one embodiment, the remote device D may be in wireless connection with a continuous blood glucose monitoring ("BGM") device G, and/or with a test strip-based BGM device S. The test strip-based BGM device S and/or the BGM device G may send data relating to the blood glucose of the patient to the remote device D. The remote device D may then communicate with the controller 24, via the wireless communication unit 27 to control the pump mechanism 20 and thereby the insulin delivery to the patient depending on e.g. the blood glucose level of the patient. For example, a blood glucose sensor as described in US20040162470A1 may be used. Alternatively, the user interface 26 can be used by the patient (X) or a health care professional ("HCP") to directly program the device 10. In addition, a health care professional HCP, the patient P or a dispensing pharmacy P may be able to upload data relating to the patient's medicament requirements, to a cloud-based server, and the remote device D may be able to communication with the cloud-based server to retrieve such information and control the operation of the device 10 accordingly. For example, a health care professional may adjust the medicament regime for a patient X depending on their latest health test or recent BGM results, and upload such data to the cloud-based server. The pharmacy P may be able to upload the specifics of the dispensed medicament to the cloud-based server, such as medicament concentration, advised delivery rate, and/or volume.

As shown in FIG. 1, the device 10 comprises an upper or reusable part 28, and a lower or disposable part 29. In use, the reusable part 28 and the disposable part 29 are assembled together. The reusable part 28 may be removably attachable to the disposable part 29, for example, when the reusable part 28 is designed to include costly components of the device 10. The reusable part 28 is mechanically connected to the disposable part 29, e.g. the reusable part 28 is clipped to the disposable part 29. The reusable part 28 is further connected to the disposable part 29 at the manifold 19, which connects the medicament reservoir 12 in the reusable part 28 to the absorbent pad 15 in the disposable part 29. In such an embodiment, a fluid coupling 37 may be provided in the manifold 19 to fluidly connect first and second sections of the manifold respectively disposed in the reusable part 28 and disposable part 29 of the device 10. Therefore, when the reusable part 28 and disposable part 29 of the device 10 are mechanically connected together as described above, the fluid coupling makes a fluid tight connection between the first and second sections of the manifold to ensure reliable delivery of the medicament from the reservoir 12 to the absorbent pad 15.

Figure 4:
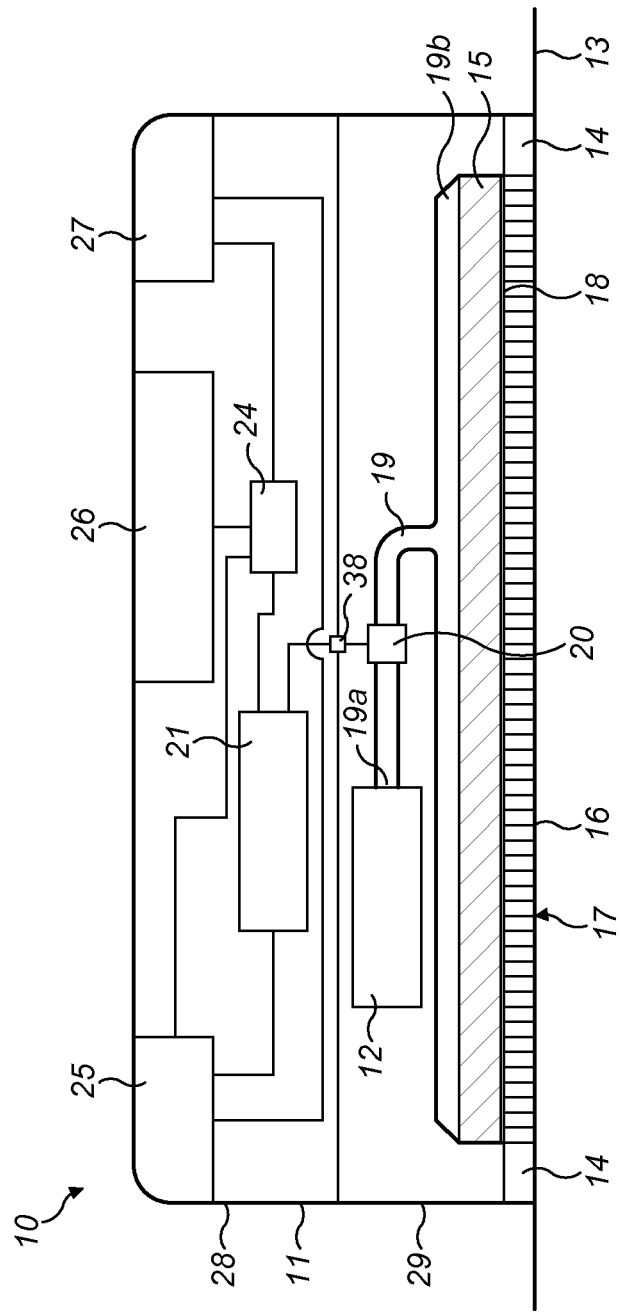
FIG. 4 is a schematic cross-sectional view of a further medicament delivery device which may include embodiments.

This arrangement of the device 10 has the advantage that the pump mechanism 20 and the delivery assembly 17 (array) can be worn together, thereby allowing to avoid the use of a separate supporting device for the pump mechanism 20. This arrangement also allows for a better control of the pump mechanism 20. In the embodiment shown in FIG. 1, the reusable part 28 includes the electronic components of the device 10, the pump mechanism 20, and the medicament reservoir 12. The disposable part 29 includes the absorbent pad 15 and the delivery assembly 17 (array). It should be noted that the invention is not intended to be limited to this particular type of device and other types of device are intended to fall within the scope of the invention. For example, as shown in FIG. 4, in an alternative embodiment, the pump mechanism 20 and the medicament reservoir 12 could be both located in the disposable part 29, and the drive motor 21 may be located in the reusable part 28. In the embodiment shown in FIG. 4, the pump mechanism 20 may be in the form of a peristaltic pump or radial pump. In such an embodiment, a mechanical coupling 38 may be provided between a drive output from the motor 21, and a drive input to the pump mechanism 20. In a further variant, the device 10 could comprise a single part, which could be either fully disposable or fully reusable.

Figure 5:
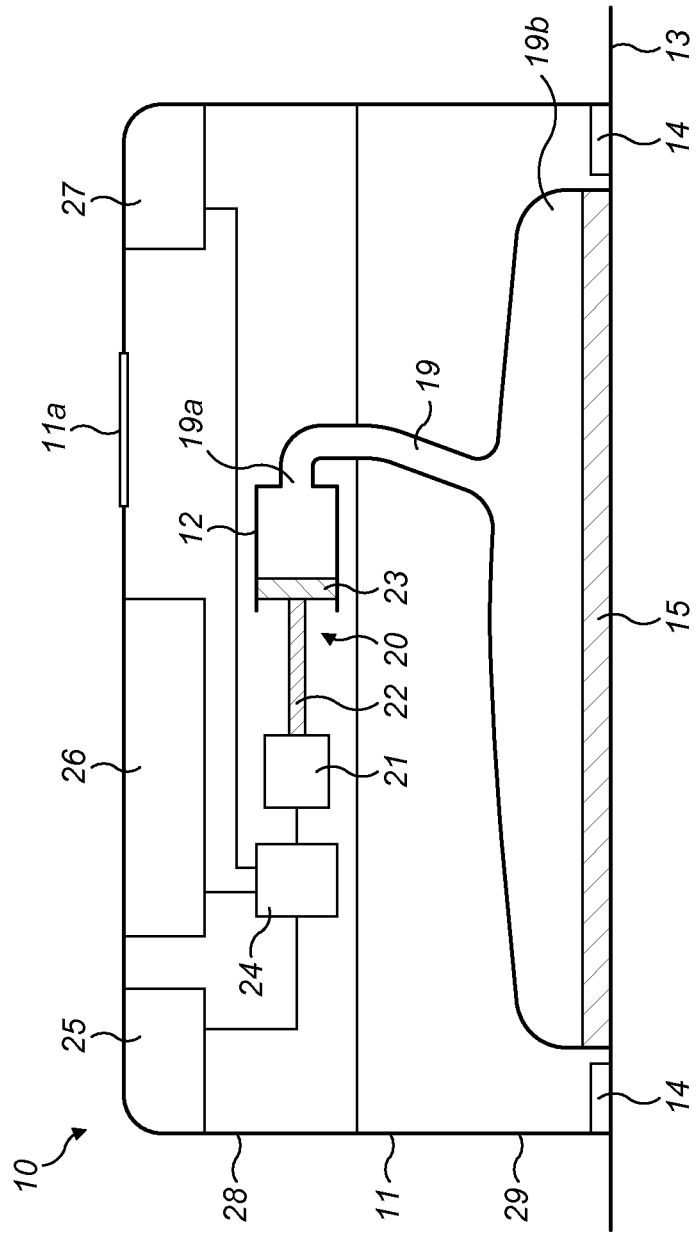
FIG. 5 is a schematic cross-sectional view of a still further medicament delivery device which may include embodiments.

The device 10 described herein comprises a delivery assembly 17 including an array of microneedles 16 for transdermally delivering medicament to the patient. However, it should be noted that the invention is not intended to be limited to this particular type of devices and other types of devices are intended to fall within the scope of the invention. For example, as shown in FIG. 5, the array of microneedles 16 can be omitted. In the embodiment shown in FIG. 5, the medicament diffuses through the skin directly from the absorbent pad 15. Such a device is particularly efficient when placed on parts of the body that are especially porous, i.e. where the skin is thin and has substantially large pores, such as the back, the shoulders, or the armpits.

The device 10 further includes a system 30 for providing information regarding the volume of medicament remaining in the device 10. The system 30 comprises a sensing unit 30a configured to measure a physical parameter dependent on the volume of medicament in the device 10. The system 30 is configured to determine the volume of medicament remaining in the device 10 based on the physical parameter measured by the sensing unit 30a.

Figure 6A:
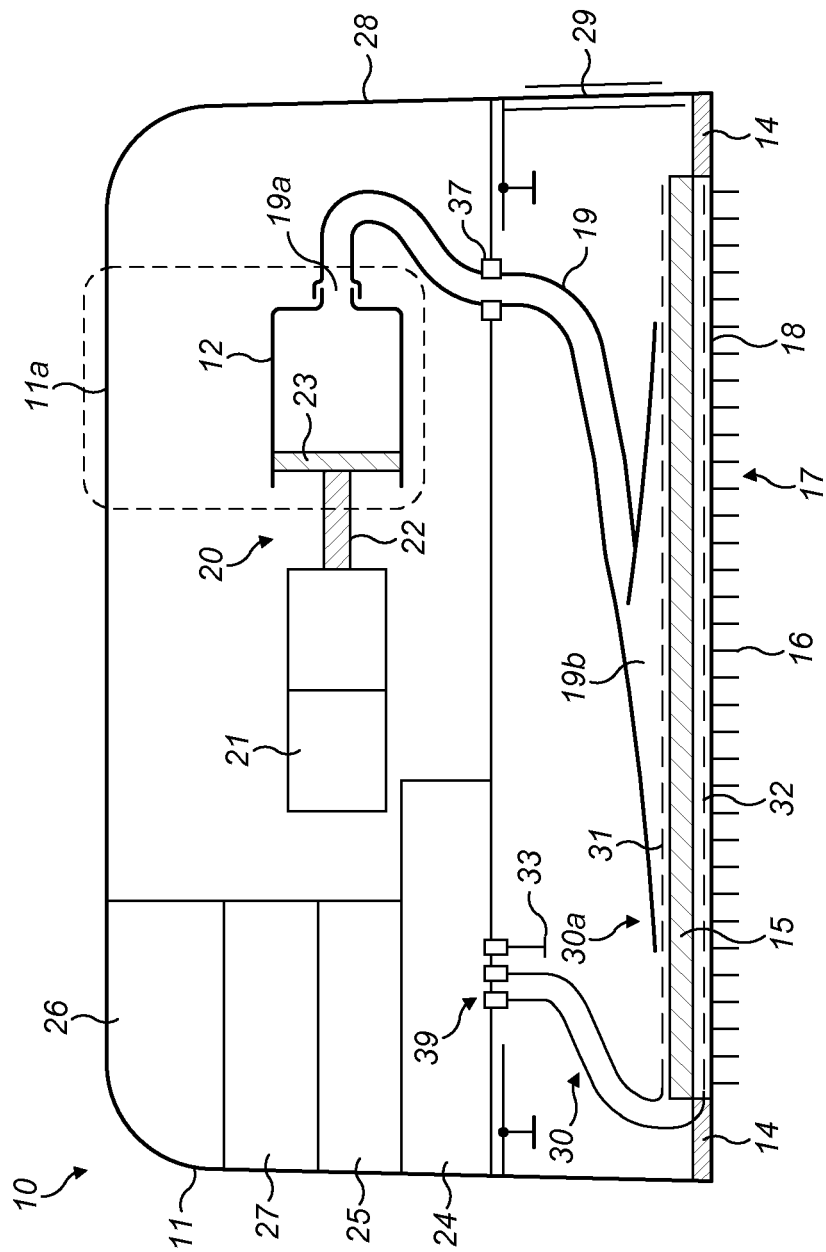
FIG. 6A is a schematic cross-sectional view of a medicament delivery device according to an embodiment.

In the embodiment shown in FIG. 6A, the sensing unit 30a comprises a first or upper electrode 31, a second or lower electrode 32, and a third or reference electrode 33. The sensing unit 30a further comprises a current source 34 connected to the first, second and third electrodes 31, 32, 33, and configured to generate a voltage between the first and second electrodes 31, 32. In the embodiment described herein, the current source 34 is a direct current source. The current source 34 may comprise the power supply 25. The electrical coupling between the reusable part 28 and the disposable part 29 may be by means of an electrical connector 39 with cooperating electrical connector elements on each of the reusable part 28 and the disposable part 29.

The upper and lower electrodes 31, 32 are in the form of metallic plates disposed substantially parallel to each other to form a capacitor. The first and second electrodes 31, 32 are disposed such that, in use, medicament flows between the first and second electrodes 31, 32. As shown in FIG. 6A, the absorbent pad 15 is arranged between the first and second electrodes 31, 32. In other words, the upper and lower electrodes 31, 32 are disposed respectively upstream and downstream of the absorbent pad 15. Alternatively, the upper and lower electrodes 31, 32 are disposed upstream of the absorbent pad 15. The upper and lower electrodes 31, 32 are disposed downstream of the dispense outlet 19b. The upper electrode 31 faces the dispense outlet 19b. The upper and lower electrode 31, 32 may advantageously be permeable such that, in use, medicament flows from the dispense outlet 19b through the upper electrode 31, the absorbent pad 15, and through the lower electrode 32 towards the microneedles 16. The lower electrode 32 is particularly advantageously permeable to allow medicament to pass through the electrode 32 to the skin. For example, the upper and lower electrodes 31, 32 are in the form of perforated plates or hole masks. The reference electrode 33 is connected to the housing 11. In use, the reference electrode 33 acts as a ground and eliminates or at least reduces noise or interferences, which may occur while the voltage between the first and second electrodes 31, 32 is measured.

The sensing unit 30a is configured to produce a direct current through the first and second electrodes 31, 32 and to measure the consequent voltage generated between the first and second electrodes 31, 32. Once the voltage is measured, the system 30 can determine the capacitance of the capacitor formed by the first and second electrodes 31, 32. When the filling level of medicament in the absorbent pad 15 changes, the amount of dielectric material between the first and second electrodes 31, 32 changes, thus producing a change in capacitance. In particular, the higher the determined capacitance, the higher the volume of medicament between the first and second electrodes 31, 32. The capacitance is determined using the following equation:

$$I(t) = C\frac{dV(t)}{dt}$$

where I is the current injected, C is the capacitance of the capacitor formed by the first and second electrodes 31, 32, and V is the voltage generated between the first and second electrodes 31, 32. The higher the permittivity of the medicament, the higher the change in capacitance, which is advantageous in the case where the device 10 is an insulin delivery device, since insulin in solution has a relative permittivity substantially high (equal to around 80, whereas e.g. plastic has a relative permittivity of around 4,5).

The device 10 may comprise an indicator configured to provide to the health care provider/professional HCP and/or to the patient information on the volume of medicament remaining in the device 10. The indicator may be configured to indicate when the volume of medicament in the device falls below a predetermined value. The indicator may be in the form of an alarm, or a display on the user interface 26. For example, the user interface 26 may display an indication that the medicament reservoir 12 needs to be changed or refilled, depending on the determined information on the volume of medicament in the device. Alternatively, or in addition, the controller 24 may transmit data to an application on a smartphone via the wireless communication unit 27 that the medicament reservoir 12 needs to be changed or refilled. This has the advantage of allowing the health care provider HCP and/or the patient to have an indication of the level of medicament remaining in the device. This may be particularly useful when an expensive medicament is being delivered, for example to verify that medicament is not leaking in the device 10.

The system 30 may be connected to the medicament pump mechanism 20 to provide feedback information on the volume of medicament in the device 10 to the medicament pump mechanism 20 so that the medicament pump mechanism 20 operates in accordance with the quantity of medicament remaining in the device 10. For example, if the system 30 determines that the volume of medicament in the device 10 falls below a predetermined value, the medicament pump mechanism 20 may stop operating.

In an alternative embodiment, the sensing unit 30a is configured to measure the resistance of the medicament between the first and second electrodes 31, 32. Since the resistance is inversely proportional to the volume of medicament between the first and second electrodes 31, 32, the system 30 can determine information on the volume of medicament between the first and second electrodes based on the measured resistance.

Figure 6B:
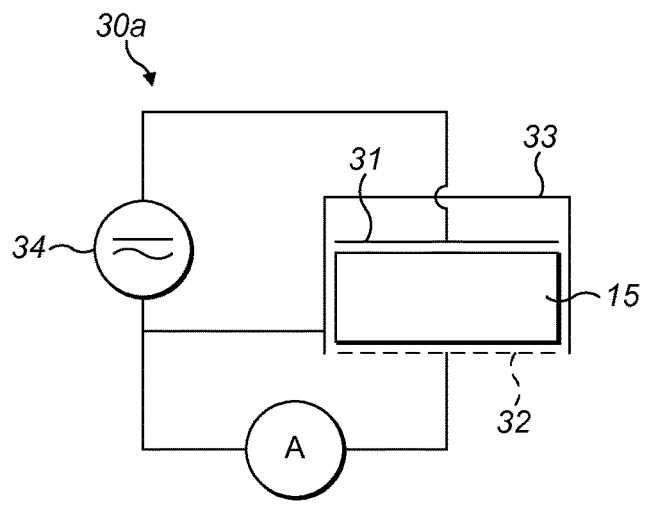
FIG. 6B is a circuit diagram of a part of the medicament delivery device of FIG. 6A.
Figure 6C:
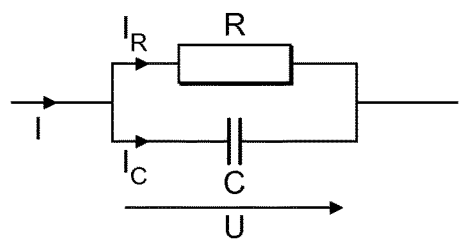
FIG. 6C is an equivalent circuit model of the medicament which, in use, flows in the device of FIG. 6A.
Figure 6D:
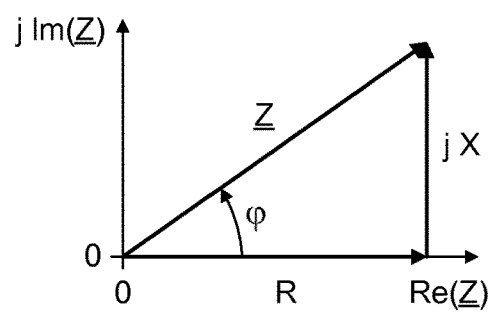
FIG. 6D is a Nyquist plot showing a complex impedance measured with the device of FIG. 6A.

In the embodiments described above, the system 30 includes a direct current source 34. However, in an alternative embodiment, the system 30 includes a source of alternating current. The sensing unit 30a is configured to measure the complex impedance of the medicament between the first and second electrodes 31, 32, e.g. by Electrochemical Impedance Spectroscopy. Based on the complex impedance measured by the sensing unit 30a, the system 30 is configured to determine information on the volume of medicament between the first and second electrodes 31, 32. In use, as shown in FIG. 6B, the alternating current source 34 supplies an alternating current e.g. in the form of a sine wave through the capacitor formed by the first and second electrodes 31, 32, and the sensing unit 30a measures the phase shift between the supplied signal and the return signal. In some embodiments, the frequency of the signal supplied may be varied to determine further information on the medicament between the first and second electrodes 31, 32. FIG. 6C shows the equivalent circuit of the medicament flowing between the first and second electrodes 31, 32, i.e. a parallel circuit composed of a resistor and a capacitor. Since the impedance is a function of the resistance and the capacitance of the medicament between the first and second electrodes 31, 32, the volume of medicament between the first and second electrodes 31, 32 can be determined based on the impedance measurement. The measured impedance may be plotted using a Nyquist plot as shown in FIG. 6D. Measuring the complex impedance allows to compensate for the effects of temperature and contact resistance in the device 10.

Impedance measurement may be performed when the device 10 is not in use, i.e. with no medicament flowing between the first and second electrodes 31, 32, in order to subtract electrodes geometry effects.

In the embodiments described above, the device 10 is described as including a system 30 configured to determine information on the volume of medicament in the device by measuring an electrical parameter in the device 10. However, the invention is not intended to be limited to this particular type of devices and other types of devices are intended to fall within the scope of the invention, for example a medicament delivery device 110 including a system 130 configured to determine information on the volume of medicament in the device by optical sensing.

Figure 7:
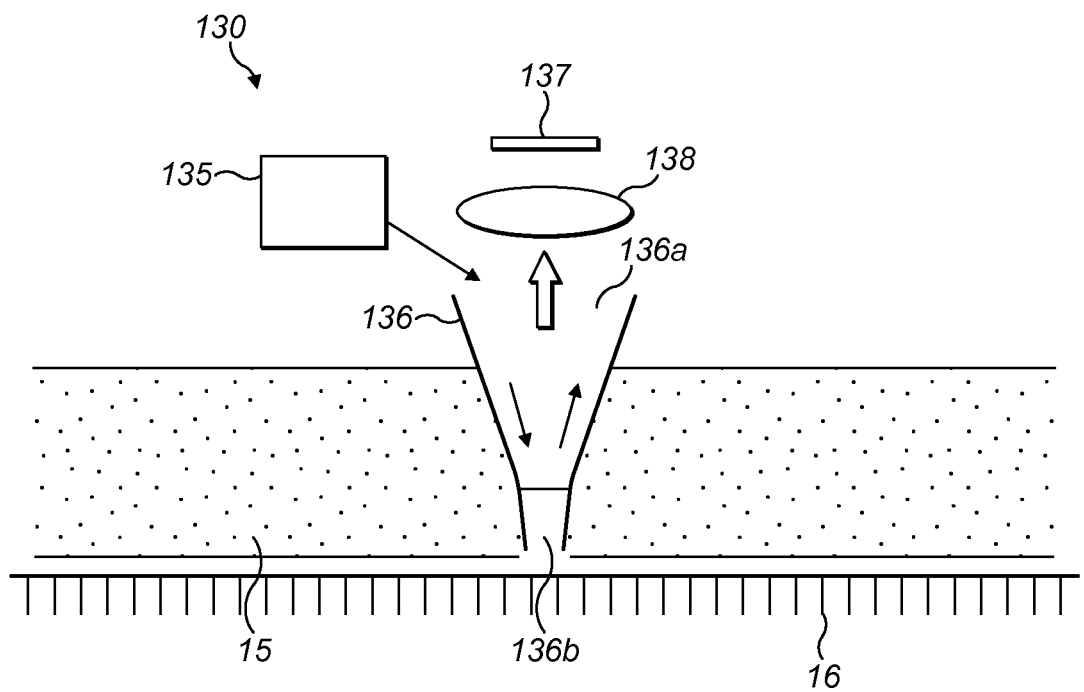
FIG. 7 is a schematic cross-sectional view of a part of a medicament delivery device according to a further embodiment.

As shown in FIG. 7, the system 130 comprises a light source 135 and a passage 136 or open-bottom receptacle or flask in which, in use, medicament can flow. The passage 136 is disposed in the absorbent pad 15. The passage 136 comprises an upper end 136a and a lower end 136b. The upper end 136a is larger than the lower end 136b such that the passage is generally funnel-shaped. The light source 135 is arranged relative to the passage 136 so that the light source 135 can emit light towards the upper end 136b. The system 130 further comprises a sensing unit 130a including an optical detector 137 and a converging lens 138. The converging lens 138 faces the upper end 136a. The converging lens 138 is disposed between the upper end 136b and the optical detector 137. In use, medicament flows from the manifold 19 towards the absorbent pad 15 in the passage 136. The light source 135 emits light towards the passage 136 filled with medicament, and the detector 137 detects light transmitted by the medicament located in the passage 136. The amount of light detected by the detector 137 depends on the amount of medicament in the passage 136, which is a function of the volume of medicament in the device 10. Therefore, the system 130 is configured to determine information on the volume of medicament in the device 110 based on the amount of light detected by the detector 137.

In the embodiments described above, the devices 10, 110 are described as including systems 30, 130 configured to determine information on the volume of medicament in the device by measuring electrical or optical parameters in the device 10. However, the invention is not intended to be limited to this particular type of medicament delivery devices and other types of devices are intended to fall within the scope of the invention, for example a medicament delivery device 210 including a system 230 configured to determine information on the volume of medicament in the device by pressure sensing.

The medicament pressure can be measured e.g. in the manifold 19. For example, the medicament pressure in the manifold 19 can be measured at two or more locations in the manifold 19. For example, a pressure difference between two locations higher than a predetermined value may indicate that medicament is leaking from the manifold 19.

Figure 8:
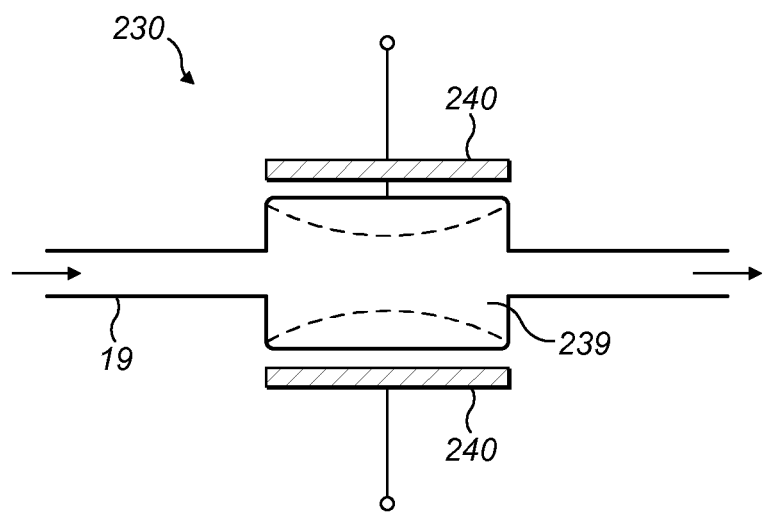
FIG. 8 is a schematic cross-sectional view of a part of a medicament delivery device according to a still further embodiment.

Alternatively, or in addition, the manifold 19 may comprise a chamber 239, as shown in FIG. 8. Depending on the manufacturing technology of the manifold 19, the chamber 239 can be integrally formed with the manifold 19 or manufactured as a separate piece that is welded to the manifold 19 in the course of manufacturing. In the unpressurized state, i.e. when the pump mechanism 20 is not operating and when medicament is not flowing in the manifold 19, the chamber 239 is collapsed (as represented by the dotted lines in FIG. 8). When the pump mechanism 20 is operating, pressure increases in the manifold 19, which widens the chamber 239. This change in pressure can be determined e.g. with an electrical capacitance measurement, by positioning a sensing unit 230a including a pair of electrodes 240 around the chamber 239, as close as possible to the wall of the chamber 239. A small amount of medicament in the chamber 239 corresponds to a low pressure, which results in a low capacitance value. In use, the chamber 239 is filled by the medicament and therefore the pressure in the chamber 239 increases, resulting in an increase of the measured capacitance. The higher the permittivity of the medicament, the higher the change in capacitance, and therefore the higher the signal to noise ratio, which is advantageous in the case where the device 10 is an insulin delivery device, since insulin in solution has a relative permittivity substantially high (equal to around 80, whereas e.g. plastic has a relative permittivity of around 4, 5). A third electrode (not shown) may be provided to act as a ground and to improve the signal to noise ratio, i.e. to eliminate or at least reduce noise or interferences, which may occur while the measurement is performed. Such capacitance measurement allows to ensure that the pump mechanism 20 does not run into the void, and also allows to verify that medicament is correctly delivered to the patient.

Figure 9:
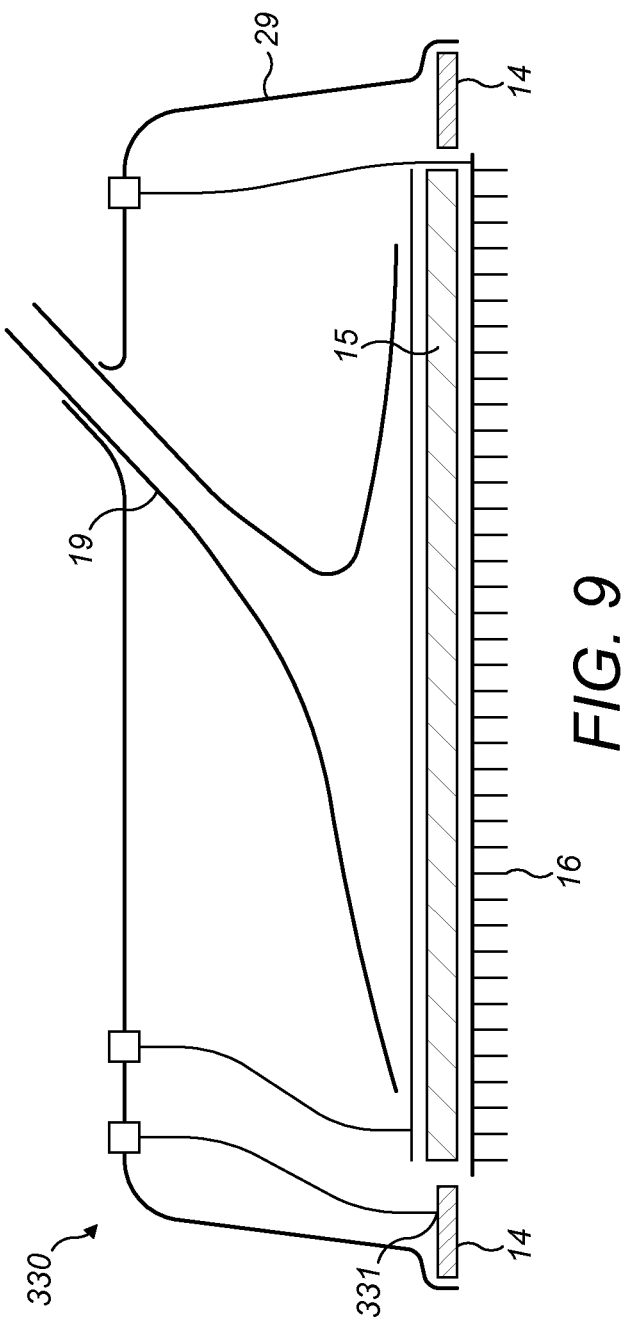
FIG. 9 is a schematic cross-sectional view of a part of a medicament delivery device according to a yet further embodiment.

As shown in FIG. 9, the devices 10, 110, 210 may comprise an assembly 330 for checking that the device 10 is correctly disposed on the skin, and in particular for checking that the contact and the pressure between the microneedles 16 and the skin are correct. The contact between the array of microneedles 16 and the skin is measured by means of an electrode arrangement comprising a first electrode 331 connected to the adhesive pad 14, and the array of electrically conductive microneedles 16 acting as a second electrode. In use, the impedance between the first electrode 331 and the array of microneedles 16 is measured. This allows to determine information on the electrical contact between the microneedles 16 and the skin. Such measure can be either performed when the device is operating, i.e. when medicament is flowing towards the array of microneedles 16, or when the device is not in use, i.e. without medicament flowing. Measuring the impedance when medicament is flowing may provide a more accurate measurement since the liquid medicament may enhance the contact between the microneedles 16 and the skin. Moreover, such measurement may provide information on the organic nature of the injection site.

Figure 10:
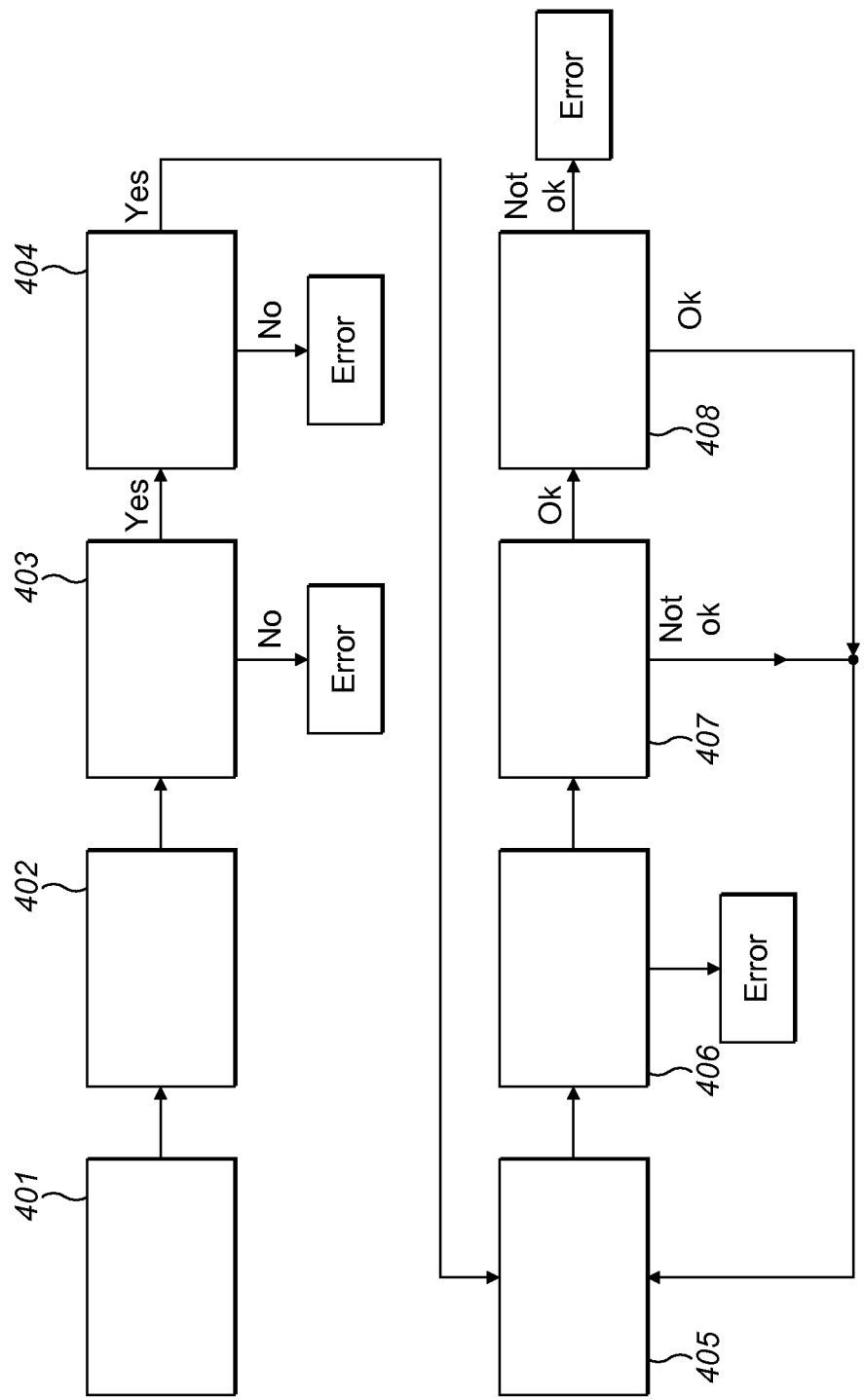
FIG. 10 is a flowchart illustrating exemplary operation of the medicament delivery device according to an embodiment.

FIG. 10 is a flow chart illustrating operation of the device according to embodiments. It will be appreciated that FIG. 10 is schematic, and omits many of the low-level details of operation of the device. The operation starts at step 401 where the reusable part 28 and the disposable part 29 are clipped or otherwise mechanically coupled together. At step 402, the reusable part 28 is turned on by activating the power supply 25, which may be by operation of the user interface 26, and which activates the controller 24 in the reusable part 28. Following step 402, one or more preliminary tests are performed in step 403, such as controls on the controller 24 functions, memories (Random Access Memory and/or Read-Only Memory), power supply 25, and/or user interface 26. These tests may also comprise checking that the medicament reservoir 12 is correctly positioned in the device, that the reservoir 12 contains enough medicament, and/or checking that the reusable part 28 and the disposable part 29 are correctly attached together, including the mechanical coupling between the reusable and disposable parts 28, 29 holding them together, the fluid coupling 37 between the first and second sections of the manifold 19, the mechanical coupling 38 between the drive output from the motor 21, and a drive input to the pump mechanism 20, and the electrical connection between the reusable part 28 and the disposable part 29 by the electrical connector 39. Yet further, the checks may detect whether the disposable part 29 has already been used, and should be replaced with a new disposable part 29 before medicament delivery can be initiated. If any of the tests at step 403 are failed, or return an incorrect result, an error message is displayed on the user interface 26. At step 404, the flow rate of the medicament to be delivered is determined depending on the patient data. As discussed above, this may be stored on the device 10 within the controller 24 memory, or may be gathered from information stored on a remote device D, received by any of the wireless communication options discussed previously. If any patient data is out of date, invalid or insufficient for safe delivery of medicament according to the intended device 10 operation, then an error message is displayed on the user interface 26. At step 405, the medicament pump mechanism 20 is activated. Then, at step 406, the pressure of medicament in the device is checked, for example, to ensure that the medicament is not leaking and that the medicament can be or is being correctly delivered to the patient. If any result of the pressure test is incorrect or not within acceptable operational parameters, an error message is displayed on the user interface 26. At step 407, the volume of medicament is determined as described above, e.g. to check that the medicament pump mechanism 20 does not run into the void and that the device is functioning correctly, for example by monitoring fluid delivery controls such as the pump mechanism 20 and motor 21. If the fluid control are not functioning, the operation loops back to step 405 to turn on the pump to activate the medicament delivery operation. If all is OK, the process moves to step 408, where the volume of medicament determined at step 407 is compared to values expected from the firmware to verify that the device is operating correctly and there is still sufficient medicament in the reservoir. If all is OK, the device operation loops back to step 405 to continue delivery of the medicament via the pump mechanism 20 and to check the ongoing fluid pressure at step 406 and medicament volume at step 407. Again, if it is detected that the device 10 is not operating correctly, the operation of the device is stopped and an error message is displayed on the user interface 26. Also, if the volume of medicament is low, it may mean that the medicament delivery process is complete and so the process stops.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals, in pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The term "drug delivery device" shall encompass any type of device or system configured to dispense a drug or medicament into a human or animal body. Without limitation, a drug delivery device may be an injection device (e.g., pen injector, auto injector, large-volume device, pump, perfusion system, or other device configured for intraocular, subcutaneous, intramuscular, or intravascular delivery), skin patch (e.g., osmotic, chemical), inhaler (e.g., nasal or pulmonary), an implantable device (e.g., drug- or API-coated stent, capsule), or a feeding system for the gastro-intestinal tract.

The drug or medicament may be contained in a primary package or "drug container" adapted for use with a drug delivery device. The drug container may be, e.g., a cartridge, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to be administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders.

Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis, and/or rheumatoid arthritis. Examples of APIs and drugs are those as described in handbooks such as Rote Liste 2014, for example, without limitation, main groups 12 (anti-diabetic drugs) or 86 (oncology drugs), and Merck index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refer to any substance that is sufficiently structurally similar to the original substance so as to have substantially similar functionality or activity (e.g., therapeutic effectiveness). In particular, the term "analogue" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can be either codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codable amino acids, or amino acids, including non-codable, have been added to the naturally occurring peptide.

Examples of insulin analogues are Gly(A21), Arg(B31), Arg(B32) human insulin (insulin glargine); Lys(B3), Glu(B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyhepta-decanoyl) human insulin.

Examples of GLP-1, GLP-1 analogues and GLP-1 receptor agonists are, for example, Lixisenatide (Lyxumia®, Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, Z'E'D-1, GSK-2374697, DA-3091, MAR-701, MAR709, ZP-2929, ZIP-3022, TT-401, BUM-034. MOD-6030, CAM-2036, DA-15864, ART-2651, ART-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berherine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigens. The antibody can be polyclonal, monoclonal, recombinant, chimeric, de-immunized or humanized, fully human, non-human, (e.g., murine), or single chain antibody. In some embodiments, the antibody has effector function and can fix a complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SHIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible fir mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit, which encompass such modifications and any and all equivalents thereof.

The invention claimed is:

1. A medicament delivery device comprising:
   a delivery assembly comprising a plurality of microneedles configured to transdermally deliver medicament to a patient;
   a system for providing information on a volume of the medicament in the medicament delivery device, the system comprising a sensing unit configured to measure at least one physical parameter dependent on the volume of the medicament in the medicament delivery device; and
   a porous membrane for retaining the medicament.

2. The medicament delivery device according to claim 1, wherein the sensing unit comprises a first electrode and a second electrode arranged to form a capacitor, wherein the first and second electrodes are configured such that the medicament flows between the first and second electrodes, wherein the sensing unit further comprises a current source connected to the first and second electrodes and configured to generate a voltage between the first and second electrodes.

3. The medicament delivery device according to claim 2, wherein the current source is a direct current source and wherein the sensing unit is configured to measure a capacitance of the capacitor formed by the first and second electrodes, and wherein the system is configured to determine information on the volume of the medicament between the first and second electrodes based on the measured capacitance.

4. The medicament delivery device according to claim 2, wherein the current source is a direct current source and wherein the sensing unit is configured to measure a resistance of the medicament between the first and second electrodes, and wherein the system is configured to determine information on the volume of the medicament between the first and second electrodes based on the measured resistance.

5. The medicament delivery device according to claim 2, wherein the current source is an alternating current source and wherein the sensing unit is configured to measure an impedance of the medicament between the first and second electrodes, and wherein the system is configured to determine information on the volume of the medicament between the first and second electrodes based on the measured impedance.

6. The medicament delivery device according to claim 2, wherein the porous membrane is disposed between the first electrode and second electrode.

7. The medicament delivery device according to claim 1, wherein the system is configured to determine information on the volume of the medicament in the medicament delivery device by optical sensing.

8. The medicament delivery device according to claim 7, wherein the system comprises:
   a light source,
   an optical detector, and
   a funnel-shaped passage configured to allow the medicament to flow therethrough,
   wherein the light source is configured to emit light towards the funnel-shaped passage when the medicament flows through the funnel-shaped passage, wherein the optical detector is configured to detect light transmitted by the medicament in the funnel-shaped passage when the medicament flows through the funnel-shaped passage, and wherein the system is configured to determine information on the volume of the medicament in the medicament delivery device based on an amount of light detected by the optical detector.

9. The medicament delivery device according to claim 1, wherein the system is configured to determine information on the volume of the medicament in the medicament delivery device by pressure sensing.

10. The medicament delivery device according to claim 1, wherein a funnel-shaped passage is located in the porous membrane.

11. The medicament delivery device according to claim 1 comprising a medicament pump mechanism configured to pump the medicament towards the delivery assembly.

12. The medicament delivery device according to claim 11, wherein the medicament pump mechanism is configured to operate based on information on the volume of the medicament in the medicament delivery device provided by the system.

13. The medicament delivery device according to claim 1, comprising a cartridge containing the medicament.

\* \* \* \* \*